United States Patent
Higashi et al.

(10) Patent No.: US 11,667,600 B2
(45) Date of Patent: *Jun. 6, 2023

(54) FLUORINATED ORGANIC COMPOUND PRODUCTION METHOD

(71) Applicants: DAIKIN INDUSTRIES, LTD., Osaka (JP); SAGA UNIVERSITY, Saga (JP)

(72) Inventors: Masahiro Higashi, Osaka (JP); Yosuke Kishikawa, Osaka (JP); Tsugio Kitamura, Saga (JP)

(73) Assignees: DAIKIN INDUSTRIES, LTD., Osaka (JP); SAGA UNIVERSITY, Saga (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/042,377

(22) PCT Filed: Mar. 29, 2019

(86) PCT No.: PCT/JP2019/014278
§ 371 (c)(1),
(2) Date: Sep. 28, 2020

(87) PCT Pub. No.: WO2019/189862
PCT Pub. Date: Oct. 3, 2019

(65) Prior Publication Data
US 2021/0024450 A1    Jan. 28, 2021

(30) Foreign Application Priority Data

Mar. 30, 2018 (JP) .............................. JP2018-067382

(51) Int. Cl.
| | | |
|---|---|---|
| *C07C 67/307* | (2006.01) | |
| *C07C 231/12* | (2006.01) | |
| *C07C 51/363* | (2006.01) | |
| *C07C 45/63* | (2006.01) | |
| *C07C 51/62* | (2006.01) | |
| *C07C 17/02* | (2006.01) | |

(52) U.S. Cl.
CPC ............ *C07C 67/307* (2013.01); *C07C 17/02* (2013.01); *C07C 45/63* (2013.01); *C07C 51/363* (2013.01); *C07C 51/62* (2013.01); *C07C 231/12* (2013.01)

(58) Field of Classification Search
None
See application file for complete search history.

(56) References Cited

U.S. PATENT DOCUMENTS

2021/0114966 A1* 4/2021 Higashi ................ C07C 67/307

FOREIGN PATENT DOCUMENTS

| JP | 10-139751 | 5/1998 |
| JP | 2009-46653 | 3/2009 |
| JP | 2014-234355 | 12/2014 |
| JP | 2015-157788 | 9/2015 |

OTHER PUBLICATIONS

Han J ("Kitamura Electrophilic Fluorination Using HF as a Source of Fluorine" Molecules 2020, 25, p. 2116) (Year: 2020).*
Han Z ("Fluorination and Fluoroalkylation Reactions Mediated by Hypervalent Iodine Reagents" Adv. Synth. Catal. 2020, 362, p. 4256-4292) (Year: 2020).*
Bafaluy ("Iodine Catalysis for C(sp3)-H Fluorination with a Nucleophilic Fluorine Source" Angew. Chem. Int. Ed. 2020, 59, p. 14241-14245) (Year: 2020).*
Kitamura ("Hypervalent Iodine-Mediated Fluorination of Styrene Derivatives" J Org Chem, 80, 2015, p. 10431-10436) (Year: 2015).*
Kitamura ("Catalytic fluorination of 1,3-dicarbonyl compounds using iodoarene catalysts" Tetrahedron Letters, 2013, 54, p. 6118-6120) (Year: 2013).*
Moriarty ("(Diacetoxyiodo)benzene" Encyclopedia of Reagents for Organic Synthesis, published Apr. 15, 2006, downloaded from https://doi.org/10.1002/047084289X.rd005m.pub2 on Jan. 21, 2022). (Year: 2006).*
Suzuki ("Iodoarene-catalyzed fluorination and aminofluorination by an Ar-I/HFpyridine/mCPBA system" Chemical Science 2014, 5, 2754-2760) (Year: 2014).*
International Search Report dated Jun. 18, 2019 in International (PCT) Application No. PCT/JP2019/014278.
Kitamura et al., "A Practical and Convenient Fluorination of 1,3-Dicarbonyl Compounds Using Aqueous HF in the Presence of Iodosylbenzene", Organic Letters, 2011, vol. 13, No. 9, pp. 2392-2394.
Kitamura et al., "Facile Synthesis of-2-Fluoro-1,3-dicarbonyl Compounds with Aqueous Hydrofluoric Acid Mediated by Iodosylarenes", Synthesis, 2013, vol. 45, No. 22, pp. 3125-3130.
Kitamura et al., "A Convenient Synthesis of 2-Fluoro- and 2-Chloromalonic Esters Mediated by Hypervalent Iodine", Synthesis, 2015, vol. 47, No. 20, pp. 3241-3245.

(Continued)

*Primary Examiner* — Amy C Bonaparte
(74) *Attorney, Agent, or Firm* — Wenderoth, Lind & Ponack, L.L.P.

(57) ABSTRACT

An object of the present invention is to provide a method for producing a fluorinated organic compound, whereby an iodosylbenzene derivative can be easily separated and recovered. The above object can be achieved by a method for producing a fluorinated organic compound, comprising step A of fluorinating an organic compound (1) by reaction with a fluorine source (3) in the presence of a hypervalent iodine aromatic ring compound (2a), or in the presence of an iodine aromatic ring compound (2b) and an oxidant (2bo); wherein the fluorine source (3) is a fluorine source (3a) represented by formula: $MF_n$, wherein M is H, a metal of Group 1 of the periodic table, or a metal of Group 2 of the periodic table; and n is 1 or 2; and step B of separating the iodine aromatic ring compound from a reaction liquid after step A is started.

5 Claims, No Drawings

(56) References Cited

OTHER PUBLICATIONS

Nash et al., "Apparent Electrophilic Fluorination of 1,3-Dicarbonyl Compounds Using Nucleophilic Fluoride Mediated by PhI(OAc)$_2$", European Journal of Organic Chemistry, 2015, vol. 2015, No. 17, pp. 3779-3786.
Extended European Search Report dated Jan. 28, 2022 in corresponding European Patent Application No. 19777301.3.

\* cited by examiner

FLUORINATED ORGANIC COMPOUND PRODUCTION METHOD

TECHNICAL FIELD

The present invention relates to a method for producing a fluorinated organic compound.

BACKGROUND ART

Fluorinated organic compounds are extremely important compounds as various chemical products, such as functional materials, pharmaceutical and agrochemical compounds, and electronic materials, as well as intermediates thereof.

Conventionally, several methods for producing fluorinated organic compounds have been proposed. For example, a known production method comprises step A of fluorinating an organic compound by bringing it into contact with (1) IF$_5$-pyridine-HF and (2) one or more additives selected from the group consisting of an amine/hydrogen fluoride salt, X$^a$F (X$^a$ representing hydrogen, potassium, sodium, or lithium), an oxidant, and a reducing agent.

CITATION LIST

Patent Literature

PTL 1: JP2015-157788A

SUMMARY OF INVENTION

Technical Problem

The present inventors found that there was room for improvement in the technique of PTL 1 in that the iodosylbenzene derivative was not separated and recovered.

An object of the present invention is to provide a method for producing a fluorinated organic compound, whereby an iodosylbenzene derivative can be easily separated and recovered.

Solution to Problem

As a result of extensive studies, the present inventors found that the above object can be achieved by a method for producing a fluorinated organic compound, comprising step A of fluorinating an organic compound (1) by reaction with a fluorine source (3)
in the presence of a hypervalent iodine aromatic ring compound (2a), or
in the presence of an iodine aromatic ring compound (2b) and an oxidant (2bo);
wherein the fluorine source (3) is a fluorine source (3a) represented by formula: MF$_n$, wherein M is H, a metal of Group 1 of the periodic table, or a metal of Group 2 of the periodic table; and n is 1 or 2; and
step B of separating the iodine aromatic ring compound from a reaction liquid after step A is started.
Thus, the present invention has been completed.

The present invention includes the following aspects.

Item 1

A method for producing a fluorinated organic compound, comprising:
step A of fluorinating an organic compound (1) by reaction with a fluorine source (3)
in the presence of a hypervalent iodine aromatic ring compound (2a), or
in the presence of an iodine aromatic ring compound (2b) and an oxidant (2bo);
wherein the fluorine source (3) is a fluorine source (3a) represented by formula: MF$_n$, wherein M is H, a metal of Group 1 of the periodic table, or a metal of Group 2 of the periodic table; and n is 1 or 2; and
step B of separating the iodine aromatic ring compound from a reaction liquid after step A is started.

Item 2

The production method according to Item 1, wherein the organic compound (1) is a carbonyl compound having a hydrogen atom, or a compound having one or more unsaturated carbon-carbon bonds.

Item 3

The production method according to Item 1 or 2, wherein the organic compound (1) is:
an organic confound represented by formula (1a):

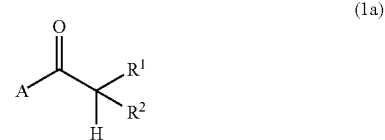

wherein
A is a hydrogen atom, an aromatic group optionally having one or more substituents, an alkyl group optionally having one or more substituents, a halogen atom, —OR, or —NR$_2$,
R$^1$ is a hydrogen atom, an organic group, or a halogen atom,
R$^2$ is a hydrogen atom, an organic group, or a halogen atom, and
R is independently at each occurrence a hydrogen atom or an organic group;
an organic compound represented by formula (1b):

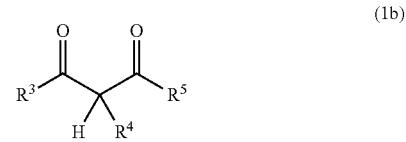

wherein
R$^3$ is a hydrogen atom, an aromatic group optionally having one or more substituents, an alkyl group optionally having one or more substituents, a halogen atom, —OR, or —NR$_2$,
R$^4$ is a hydrogen atom, an aromatic group optionally having one or more substituents, an alkyl group optionally having one or more substituents, a halogen atom, —OR, or —NR$_2$,
R$^5$ is a hydrogen atom, an aromatic group optionally having one or more substituents, an alkyl group optionally having one or more substituents, a halogen atom, —OR, or —NR$_2$,
and R is independently at each occurrence a hydrogen atom or an organic group; or an organic compound represented by formula (1c):

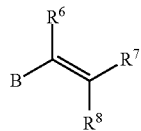

(1c)

wherein
B is an aromatic group optionally having one or more substituents, or an alkyl group optionally having one or more substituents,
$R^6$ is a hydrogen atom, an organic group, or a halogen atom,
$R^7$ is a hydrogen atom, an organic group, or a halogen atom, and
$R^8$ is a hydrogen atom, an organic group, or a halogen atom.

Item 4

The production method according to any one of Items 1 to 3, wherein the hypervalent iodine aromatic ring compound. (2a) is an organic compound represented by formula (2a1):

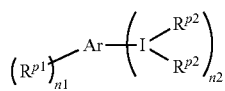

(2a1)

wherein
Ar is an aromatic ring,
$R^{p1}$ is independently at each occurrence
  an alkyl group,
  an alkoxy group,
  a group: —O—$(CH_2)_q$—$NR_3X$, wherein q is a number greater than or equal to 1; K is H or a $C_1$-$C_{20}$ alkyl group; and X is a halogen atom, an arylsulfonyloxy group, or an alkylsulfonyloxy group,
  a group: —$(CH_2)_q$—$NR_3X$, wherein q is a number greater than or equal to 1; R is H or a $C_1$-$C_{10}$ alkyl group; and X is a halogen atom, an arylsulfonyloxy group, or an alkylsulfonyloxy group,
  a group: —O—$(CH_2)_q$-A, wherein A is —$SO_3Y$ or —COOY; Y is independently at each occurrence H, a metal atom, or $NR^5_4$; and $R^5$ is independently at each occurrence H or an organic group,
  a group: —$(CH_2)_q$-A wherein A is —$SO_3Y$ or —COOY; Y is independently at each occurrence H, a metal atom, or $NR^5_4$; and $R^5$ is independently at each occurrence H or an organic group,
  a halogen atom,
  a cyano group,
  a nitre group,
  a carboxylic acid group, or
  a sulfonic acid group;
$R^{p2}$ is independently at each occurrence
  an alkyl group,
  an alkoxy group,
  a group: —O—$(CH_2)_q$—$NR_3X$, wherein q is a number greater than or equal to 1; R is H or a $C_1$-$C_{20}$ alkyl group; and X is a halogen atom, an arylsulfonyloxy group, or an alkylsulfonyloxy group,
  a group: —O—$(CH_2)_q$—$NR_3X$, wherein q is a number greater than or equal to 1; R is H or a $C_1$-$C_{20}$ alkyl group and X is a halogen atom, an arylsulfonyloxy group, or an alkylsulfonyloxy group,
  a halogen atom,
  a cyano group,
  a nitro group,
  a carboxylic acid group,
  a sulfonic acid group,
  a hydroxy group, or
  a phosphoryloxy group; or
two $R^{p2}$ bonded to one iodine atom optionally together form =O;
n1 is a number greater than or equal to 0;
n2 is a number greater than or equal to 1; and
the sum of n1 and n2 is in the range of 1 to 11; and
the iodine aromatic ring compound (2b) is an organic compound represented by formula (2b1):

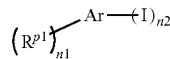

(2b1)

wherein
Ar is an aromatic ring;
$R^{p1}$ is independently at each occurrence
  an alkyl group,
  an alkoxy group,
  a group; —O—$(CH_2)_q$—$NR_3X$, wherein q is a number greater than or equal to 1; R is H or a $C_1$-$C_{20}$ alkyl group; and X is a halogen atom, an arylsolfonyloxy group, or an alkylsolfonyloxy group,
  a group: —$(CH_2)_q$—$NR_3X$, wherein q is a number greater than or equal to 1; R is H or a $C_1$-$C_{20}$ alkyl group; and X is a halogen atom, an arylsulfonyloxy group, or an alkylsulfonyloxy group,
  a group: —O—$(CH_2)_q$-A, wherein A is —$SO_3Y$ or —COOY; Y is independently at each occurrence H, a metal atom, or $NR^5_4$; and $R^5$ is independently at each occurrence H or an organic group,
  a group: —$(CH_2)_q$-A, wherein A is —$SO_3Y$ or —COOY; Y is independently at each occurrence H, a metal atom, or $NR^5_4$; and $R^5$ is independently at each occurrence H or an organic group,
  a halogen atom,
  a cyano group,
  a nitro group,
  a carboxylic acid group, or
  a sulfonic acid group;
n1 is a number greater than or equal to 0;
n2 is a number greater than or equal to 1; and
the sum of n1 and n2 is in the range of 1 to 11.

Item 5

The production method according to Item 4, wherein in formulas (2a1) and (2b1) is independently at each occurrence, an alkyl group optionally substituted with one or more fluorine atoms, an alkoxy group optionally substituted with one or more fluorine atoms, a halogen atom, a carboxylic acid group, or a sulfonic acid group.

Item 6

The production method according to Item 4 or 5, wherein $R^{p2}$ in formula (p1) is independently at each occurrence a halogen atom, an acetic acid group, a trifluoroacetic acid group, a tosic acid group, a hydroxy group, a phosphoryloxy group, a trifluoromethanesulfonic acid group, a propionic acid group, a 3,3,3-trifluorapropionic acid group, a perfluoropropionic acid group, a perfluorobutyric acid group, or a methanesulfonic acid group.

Item 7

The production method according to any one of Items 1 to 6, wherein the oxidant (1bo) is one or more members selected from the group consisting of metachloroperbenzoic acid, hydrogen peroxide, peracetic acid, perbenzoic acid, tert-butyl hydroperoxide, cumene hydroperoxide, potassium persulfate, and a potassium hydrogen persulfate-potassium hydrogen sulfate-potassium sulfate mixture.

Item 8

The production method according to any one of Items 1 to 7, comprising step C of oxidizing the iodine-substituted aromatic ring compound separated from the reaction liquid in step B with an oxidant (C).

Item 9

The method according to Item 8, wherein the oxidant (C) is one or more members selected from the group consisting of metachloroperbenzoic acid, hydrogen peroxide, peracetic acid, perbenzoic acid, tert-butyl hydroperoxide, cumene hydroperoxide, potassium persulfate, and a potassium hydrogen persulfate-potassium hydrogen sulfate-potassium sulfate mixture.

Advantageous Effects of Invention

The present invention provides a novel method for producing a fluorinated organic compound.

In the production method of the present invention, an iodine aromatic ring compound is recovered.

DESCRIPTION OF EMBODIMENTS

1. Term

The symbols and abbreviations in the present specification can be understood in the sense commonly used in the technical field to which the present invention pertains in the context of the present specification, unless otherwise specified.

In the present specification, the terms "comprise" and "contain" are used with the intention of including the phrases "consist essentially of" and "consist of."

Unless otherwise specified, the steps, treatments, or operations described in the present specification may be performed at room temperature.

In the present specification, room temperature can mean a temperature in the range of 10 to 40° C.

In the present specification, the phrase "$C_n$-$C_m$" (wherein n and m each represent a number) indicates that the number of carbon atoms is n or more and m or less, as a person skilled in the art would generally understand.

In the present specification, examples of the "metal atom" include:
metals of Group 1 of the periodic table (e.g., lithium, sodium, and potassium); metals of Group 2 of the periodic table (e.g., magnesium and calcium); transition metals of Group 4 (e.g., scandium, titanium, vanadium, chromium, manganese, iron, cobalt, nickel, and copper); metals of Group 12 (e.g., zinc, cadmium, and mercury); and metals of Group 13 (e.g., aluminum, gallium, and indium).

In the present specification, the phrase "organic compound" is understood in the ordinary sense and can be a compound having one or more carbon atoms and one or more hydrogen atoms.

In the present specification, the fluorinated organic compound refers to a compound that can be produced by fluorinating an organic compound, and may not contain a hydrogen atom.

In the present specification, unless otherwise specified, examples of the "halo (group)" may include fluoro (group), chloro (group), bromo (group), and iodine (group).

In the present specification, unless otherwise specified, examples of the "halogen (atom)" may include fluorine (atom), chlorine (atom), bromine (atom), and iodine (atom).

In the present specification, examples of the "aromatic ring" include aromatic carbon rings and aromatic heterocyclic rings.

In the present specification, the "aromatic ring compound" refers to a compound having one or more aromatic rings.

In the present specification, unless otherwise specified, examples of the "aromatic carbon rings" include aromatic hydrocarbon rings having 6 to 14 carbon atoms, and specific examples include benzene, naphthalene, anthracene, phenanthrene, and biphenyl.

In the present specification, unless otherwise specified, examples of the "aromatic heterocyclic rings" include 5- or 6-membered aromatic heterocyclic rings, and specific examples include a furan ring, a thiophene ring, a pyrrole ring, an oxazole ring, an isoxazole ring, a thiazole ring, an isothiazole ring, an imidazole ring, a pyrazole ring, a 1,2,3-oxadiazole ring, a 1,2,4-oxadiazole ring, a 1,3,4-oxadiazole ring, a furazan ring, a 1,2,3-thiadiazole ring, a 1,2,4-thiadiazole ring, a 1,3,4-thiadiazole ring, a 1,2,3-triazole ring, a 1,2,4-triazole ring, a tetrazole ring, a pyridine ring, a pyridazine ring, a pyrimidine ring, a pyrazine ring, and a triazine ring.

In the present specification, unless otherwise specified, other examples of the "aromatic heterocyclic rings" include a condensed ring of one or more 5- or 6-membered aromatic heterocyclic rings and one or more aromatic carbon rings.

In the present specification, the "organic group" refers to a group containing one or more carbon atoms (or a group formed by removing one hydrogen atom from an organic compound).

Examples of the "organic group" may include:
an alkyl group optionally having one or more substituents,
an alkenyl group optionally having one or more substituents,
an alkynyl group optionally having one or more substituents,
a cycloalkyl group optionally having one or more substituents,
a cycloalkenyl group optionally having one or more substituents,
a cycloalkadienyl group optionally having one or more substituents,
an aryl group optionally having one or more substituents,
an aralkyl group optionally having one or more substituents,
a non-aromatic heterocyclic group optionally having one or more substituents,
a heteroaryl group optionally having one or more substituents, a cyano group,
an aldehyde group,
R'O—,
R'CO—,
R'SO$_2$—,
R'OCO—, and
R'OSO$_2$—
(in these formulas, R' is independently
an alkyl group optionally having one or more substituents,
an alkenyl group optionally having one or more substituents,
an alkynyl group optionally having one or more substituents,
a cycloalkyl group optionally having one or more substituents,
a cycloalkenyl group optionally having one or more substituents,
a cycloalkadienyl group optionally having one or more substituents,
an aryl group optionally having one or more substituents,
an aralkyl group optionally having one or more substituents,
a non-aromatic heterocyclic group optionally having one or more substituents, or
a heteroaryl group optionally having one or more substituents.)

In the present specification, the "organic group" may be, for example, a hydrocarbon group optionally having one or more substituents, wherein to the hydrocarbon group, one or more moieties selected from the group consisting of —NR$^o$—, =N—, —N=, —O—, —S—, —C(=O)O—, —OC(=O)—, —C(=O)—, —S(=O)—, —S(=O)$_2$—, —S(=O)$_2$—NR$^o$—, —NR$^o$—S(=O)$_2$—, —S(=O)—NR$^o$—, and —NR$^o$—S(=O)— (in these formulas, R$^o$ is independently a hydrogen atom or an organic group) may be inserted.

As is generally understood based on common knowledge in the field of chemistry, examples of the hydrocarbon group with a heteroatom thus inserted may include non-aromatic heterocyclic groups and heteroaryl groups.

In the present specification, the number of carbon atoms in the "hydrocarbon group" of the "hydrocarbon group optionally having one or more substituents" may be, for example, 1 to 100, 1 to 80, 1 to 60, 1 to 40, 1 to 30, 1 to 20, or 1 to 10 (e.g., 1, 2, 3, 4, 5, 6, 7, 8, 9, or 10).

In the present specification, examples of the "substituents" in the "hydrocarbon group optionally having one or more substituents," "alkyl group optionally having one or more substituents," "alkenyl group optionally having one or more substituents," "alkynyl group optionally having one or more substituents," "cycloalkyl group optionally having one or more substituents," "cycloalkenyl group optionally having one or more substituents," "cycloalkadienyl group optionally having one or more substituents," "aryl group optionally having one or more substituents," and "aralkyl group optionally having one or more substituents" may include a halo group, a nitro group, a cyano group, an oxo group, a thioxo group, a sulfo group, a sulfamoyl group, a sulfinamoyl group, and a sulfenamoyl group.

The number of substituents may be in the range of 1 to the maximum substitutable number (e.g., 1, 2, 3, 4, 5, or 6).

In the present specification, examples of the "hydrocarbon group" may include an alkyl group, an alkenyl group, an alkynyl group, a cycloalkyl group, a cycloalkenyl group, a cycloalkadienyl group, an aryl group, an aralkyl group, and a group that is a combination of these groups.

In the present specification, unless otherwise specified, examples of the "alkyl group" may include linear or branched C$_1$-C$_{10}$ alkyl groups, such as methyl, ethyl, propyl, isopropyl, butyl, isobutyl, sec-butyl, tert-butyl, pentyl, isopentyl, neopentyl, hexyl, heptyl, octyl, nonyl, and decyl.

In the present specification, the "fluoroalkyl group" is an alkyl group in which at least one hydrogen atom is replaced by a fluorine atom.

In the present specification, the number of fluorine atoms in the "fluoroalkyl group" may be 1 or more (e.g., 1 to 3, 1 to 6, 1 to 12, or 1 to the maximum substitutable number).

As a person skilled in the art would generally understand, the suffix "perhalogeno" means that all hydrogen atoms are replaced by halo groups.

As a person skilled in the art would generally understand, the suffix "perfluoro" means that all hydrogen atoms are replaced by fluoro groups.

The "fluoroalkyl group" includes a perfluoroalkyl group.

The "perfluoroalkyl group" is an alkyl group in which all hydrogen atoms are replaced by fluorine atoms. Specific examples of the perfluoroalkyl group include a trifluoromethyl group (CF$_3$—) and a pentafluoroethyl group (C$_2$F$_5$—).

In the present specification, the "fluoroalkyl group" may be, for example, a fluoroalkyl group having 1 to 20, 1 to 12, 1 to 6, 1 to 4, 1 to 3, 6, 5, 4, 3, 2, or 1 carbon atom.

In the present specification, the "fluoroalkyl group" may be a linear or branched fluoroalkyl group.

In the present specification, specific examples of the "fluoroalkyl group" include a fluoromethyl group, a difluoromethyl group, a trifluoromethyl group (CF$_3$—), a 2,2,2-trifluoroethyl group, a pentafluoroethyl group (C$_2$F$_5$—), a tetrafluoropropyl group (e.g., HCF$_2$CF$_2$CH$_2$—), a hexafluoropropyl group (e.g., (CF$_3$)$_2$CH—), a nonafluorobutyl group, an octafluoropentyl group (e.g., HCF$_2$CF$_2$CF$_2$CF$_2$CH$_2$—), a tridecafluorohexyl group, a 3,3,4,4,5,5,6,6,7,7,8,8,8-tridecafluorooctyl group (CF$_3$CF$_2$CF$_2$CF$_2$CF$_2$CF$_2$CH$_2$CH$_2$—), and the like.

In the present specification, unless otherwise specified, examples of the "alkenyl group" may include linear or branched C$_{2-10}$ alkenyl groups, such as vinyl, 1-propen-1-yl, 2-propen-1-yl, isopropenyl, 2-buten-1-yl, 4-penten-1-yl, and 5-hexen-1-yl.

In the present specification, unless otherwise specified, examples of the "alkynyl group" may include linear or branched C$_2$-C$_{10}$ alkynyl groups, such as ethynyl, 1-propyn-1-yl, 2-propyn-1-yl, 4-pentyn-1-yl, and 5-hexyn-1-yl.

In the present specification, unless otherwise specified, examples of the "cycloalkyl group" may include C$_3$-C$_7$ cycloalkyl groups, such as cyclopropyl, cyclobutyl, cyclopentyl, cyclohexyl, and cycloheptyl.

In the present specification, unless otherwise specified, examples of the "cycloalkenyl group" may include C$_3$-C$_7$ cycloalkenyl groups, such as cyclopropenyl, cyclobutenyl, cyclopentenyl, cyclohexenyl, and cycloheptenyl.

In the present specification, unless otherwise specified, examples of the "cycloalkadienyl group" may include C$_4$-C$_{10}$ cycloalkadienyl groups, such as cyclobutadienyl, cyclopentadienyl, cyclohexadienyl, cycloheptadienyl, cyclooctadienyl, cyclononadienyl, and cyclodecadienyl.

In the present specification, unless otherwise specified, the aromatic group includes an "aryl group" and a "heteroaryl group."

In the present specification, unless otherwise specified, the "aryl group" may be monocyclic, bicyclic, tricyclic, or tetracyclic.

In the present specification, unless otherwise specified, the "aryl group" may be a C$_6$-C$_{18}$ aryl group.

In the present specification, unless otherwise specified, examples of the "aryl group" may include phenyl, 1-naphthyl, 2-naphthyl, 2-biphenyl, 3-biphenyl, 4-biphenyl, and 2-anthryl.

In the present specification, unless otherwise specified, examples of the "aralkyl group" may include benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylylmethyl, 3-biphenylylmethyl, and 4-biphenylylmethyl.

In the present specification, unless otherwise specified, the "non-aromatic heterocyclic group" may be monocyclic, bicyclic, tricyclic, or tetracyclic.

In the present specification, unless otherwise specified, the "non-aromatic heterocyclic group" may be, for example, a non-aromatic heterocyclic group that contains, as a ring-constituting atom(s), 1 to 4 heteroatoms selected from an oxygen atom, a sulfur atom, and a nitrogen atom, in addition to a carbon atom.

In the present specification, unless otherwise specified, the "non-aromatic heterocyclic group" may be saturated or unsaturated.

In the present specification, unless otherwise specified, examples of the "non-aromatic heterocyclic group" may include tetrahydrofuryl, oxazolidinyl, imidazolinyl (e.g., 1-imidazolinyl, 2-imidazolinyl, and 4-imidazolinyl), aziridinyl (e.g., 1-aziridinyl and 2-aziridinyl), azetidinyl (e.g., 1-azetidinyl and 2-azetidinyl), pyrrolidinyl (e.g., 1-pyrrolidinyl, 2-pyrrolidinyl, and 3-pyrrolidinyl), piperidinyl (e.g., 1-piperidinyl, 2-piperidinyl, and 3-piperidinyl), azepanyl (e.g., 1-azepanyl, 2-azepanyl, 3-azepanyl, and 4-azepanyl), azocanyl (e.g., 1-azocanyl, 2-azocanyl, 3-azocanyl, and 4-azocanyl), piperazinyl (e.g., 1,4-piperazin-1-yl and 1,4-piperazin-2-yl), diazepinyl (e.g., 1,4-diazepin-1-yl, 1,4-diazepin-2-yl, 1,4-diazepin-5-yl, and 1,4-diazepin-6-yl), diazocanyl (e.g., 1,4-diazocan-1-yl, 1,4-diazocan-2-yl, 1,4-diazocan-5-yl, 1,4-diazocan-6-yl, 1,5-diazocan-1-yl, 1,5-diazocan-2-yl, and 1,5-diazocan-3-yl), tetrahydropyranyl (e.g., tetrahydropyran-4-yl), morpholinyl (e.g., 4-morpholinyl), thiomorpholinyl (e.g., 4-thiomorpholinyl), 2-oxazolidinyl, dihydrofuryl, dihydropyranyl, dihydroquinolyl, and the like.

In the present specification, unless otherwise specified, examples of the "heteroaryl group" may include monocyclic aromatic heterocyclic groups (e.g., 5- or 6-membered monocyclic aromatic heterocyclic groups) and aromatic condensed heterocyclic groups (e.g., 5- to 18-membered aromatic condensed heterocyclic groups).

In the present specification, unless otherwise specified, examples of the "5- or 6-membered monocyclic aromatic heterocyclic groups" may include pyrrolyl (e.g., 1-pyrrolyl, 2-pyrrolyl, and 3-pyrrolyl), furyl (e.g., 2-furyl and 3-furyl), thienyl (e.g., 2-thienyl and 3-thienyl), pyrazolyl (e.g., 1-pyrazolyl, 3-pyrazolyl, and 4-pyrazolyl), imidazolyl (e.g., 1-imidazolyl, 2-imidazolyl, and 4-imidazolyl), isoxazolyl (e.g., 3-isoxazolyl, 4-isoxazolyl, and 5-isoxazolyl), oxazolyl (e.g., 2-oxazolyl, 4-oxazolyl, and 5-oxazolyl), isothiazolyl (e.g., 3-isothiazolyl, 4-isothiazolyl, and 5-isothiazolyl), thiazolyl (e.g., 2-thiazolyl, 4-thiazolyl, and 5-thiazolyl), triazolyl (e.g., 1,2,3-triazol-4-yl and 1,2,4-triazol-3-yl), oxadiazolyl (e.g., 1,2,4-oxadiazol-3-yl and 1,2,4-oxadiazol-5-yl), thiadiazolyl (e.g., 1,2,4-thiadiazol-3-yl and 1,2,4-thiadiazol-5-yl), tetrazolyl, pyridyl (e.g., 2-pyridyl, 3-pyridyl, and 4-pyridyl), pyridazinyl (e.g., 3-pyridazinyl and 4-pyridazinyl), pyrimidinyl (e.g., 2-pyrimidinyl, 4-pyrimidinyl, and 5-pyrimidinyl), pyrazinyl, and the like.

In the present specification, unless otherwise specified, examples of the "5- to 18-membered aromatic condensed heterocyclic groups" may include isoindolyl (e.g., 1-isoindolyl, 2-isoindolyl, 3-isoindolyl, 4-isoindolyl, 5-isoindolyl, 6-isoindolyl, and 7-isoindolyl), indolyl (e.g., 1-indolyl, 2-indolyl, 3-indolyl, 4-indolyl, 5-indolyl, 6-indolyl, and 7-indolyl), benzo[b]furanyl (e.g., 2-benzo[b]furanyl, 3-benzo[b]furanyl, 4-benzo[b]furanyl, 5-benzo[b]furanyl, 6-benzo[b]furanyl, and 7-benzo[b]furanyl), benzole[c]furanyl (e.g., 1-benzo[c]furanyl, 4-benzo[c]furanyl, and 5-benzo[c]furanyl), benzo[b]thienyl (e.g., 2-benzo[b]thienyl, 3-benzo[b]thienyl, 4-benzo[b]thienyl, 5-benzo[b]thienyl, 6-benzo[b]thienyl, and 7-benzo[b]thienyl), benzo[c]thienyl (e.g., 1-benzo[c]thienyl, 4-benzo[c]thienyl, and 5-benzo[c]thienyl), indazolyl (e.g., 1-indazolyl, 2-indazolyl, 3-indazolyl, 4-indazolyl, 5-indazolyl, 6-indazolyl, and 7-indazolyl), benzimidazolyl (e.g., 1-benzimidazolyl, 2-benzimidazolyl, 4-benzimidazolyl, and 5-benzimidazolyl), 1,2-benzisoxazolyl (e.g., 1,2-benzisoxazol-3-yl, 1,2-benzisoxazol-4-yl, 1,2-benzisoxazol-5-yl, 1,2-benzisoxazol-6-yl, and 1,2-benzisoxazol-7-yl), benzoxazolyl (e.g., 2-benzoxazolyl, 4-benzoxazolyl, 5-benzoxazolyl, 6-benzoxazolyl, and 7-benzoxazolyl), 1,2-benzisothiazolyl (e.g., 1,2-benzisothiazol-3-yl, 1,2-benzisothiazol-4-yl, 1,2-benzisothiazol-5-yl, 1,2-benzisothiazol-6-yl, and 1,2-benzisothiazol-7-yl), benzothiazolyl (e.g., 2-benzothiazolyl, 4-benzothiazolyl, 5-benzothiazolyl, 6-benzothiazolyl, and 7-benzothiazolyl), isoquinolyl (e.g., 1-isoquinolyl, 3-isoquinolyl, 4-isoquinolyl, and 5-isoquinolyl), quinolyl (e.g., 2-quinolyl, 3-quinolyl, 4-quinolyl, 5-quinolyl, and 8-quinolyl), cinnolinyl (e.g., 3-cinnolinyl, 4-cinnolinyl, 5-cinnolinyl, 6-cinnolinyl, 7-cinnolinyl, and 8-cinnolinyl), phthalazinyl (e.g., 1-phthalazinyl, 4-phthalazinyl, 5-phthalazinyl, 6-phthalazinyl, 7-phthalazinyl, and 8-phthalazinyl), quinazolinyl (e.g., 2-quinazolinyl, 4-quinazolinyl, 5-quinazolinyl, 6-quinazolinyl, 7-quinazolinyl, and 8-quinazolinyl), quinoxalinyl (e.g., 2-quinoxalinyl, 3-quinoxalinyl, 5-quinoxalinyl, 6-quinoxalinyl, 7-quinoxalinyl, and 8-quinoxalinyl), pyrazolo[1,5-a]pyridyl (e.g., pyrazolo[1,5-a]pyridin-2-yl, pyrazolo[1,5-a]pyridin-3-yl, pyrazolo[1,5-a]pyridin-4-yl, pyrazolo[1,5-a]pyridin-5-yl, pyrazolo[1,5-a]pyridin-6-yl, and pyrazolo[1,5-a]pyridin-7-yl), imidazo[1,2-a]pyridyl (e.g., imidazo[1,2-a]pyridin-2-yl, imidazo[1,2-a]pyridin-3-yl, imidazo[1,2-a]pyridin-5-yl, imidazo[1,2-a]pyridin-6-yl, imidazo[1,2-a]pyridin-7-yl, and imidazo[1,2-a]pyridin-8-yl), and the like In the present specification, unless otherwise specified, examples of the "substituents" in the "non-aromatic heterocyclic group optionally having one or more substituents" and "heteroaryl group optionally having one or more substituents" may include a hydrocarbon group optionally having one or more substituents, a halo group, a nitro group, a cyano group, an oxo group, a thioxo group, a sulfo group, a sulfamoyl group, a sulfinamoyl group, and a sulfenamoyl group.

The number of substituents may be in the range of 1 to the maximum substitutable number (e.g., 1, 2, 3, 4, 5, or 6).

2. Method for Producing a Fluorinated Organic Compound

The method for producing a fluorinated organic compound according to the present invention comprises:
step A of fluorinating an organic compound (1) by reaction with a fluorine source (3)
in the presence of a hypervalent iodine aromatic ring compound (2a), or in the presence of an iodine aromatic ring compound (2b) and an oxidant (2bo); and step B of separating the iodine aromatic ring compound (2b) from a reaction liquid after step A is started.

2.1. Substrate

The organic compound (1), which is the substrate of the production method of the present invention, may be preferably a carbonyl compound having a hydrogen atom, or a compound having one or more unsaturated carbon-carbon bonds.

Just for the sake of confirmation, the organic compound (1) may have one or more fluorine atoms.

Preferable examples of the organic compound (1) include: a compound represented by formula (1a):

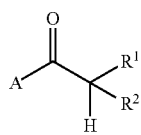
(1a)

wherein
A is a hydrogen atom, an aromatic group optionally having one or more substituents, an alkyl group optionally having one or more substituents, a halogen atom, —OR, or —NR$_2$,
$R^1$ is a hydrogen atom, an organic group, or a halogen atom,
$R^2$ is a hydrogen atom, an organic group, or a halogen atom, and
R is independently at each occurrence a hydrogen atom or an organic group;
a compound represented by formula (1b):

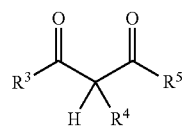
(1b)

wherein
$R^3$ is a hydrogen atom, an aromatic group optionally having more substituents, an alkyl group optionally having one or substituents, a halogen atom, —OR, or —NR$_2$,
$R^4$ is a hydrogen atom, an aromatic group optionally having one or more substituents, an alkyl group optionally having one or more substituents, a halogen atom, —OR, or —NR$_2$,
$R^5$ is a hydrogen atom, an aromatic group optionally having one or more substituents, an alkyl group optionally having one or more substituents, a halogen atom, —OR, or —NR$_2$, and
R is independently at each occurrence a hydrogen atom or an organic group; or
a compound represented by formula (1c):

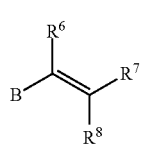
(1c)

wherein
B is an aromatic group optionally having one or more substituents, or an alkyl group optionally having one or more substituents,
$R^6$ is a hydrogen atom, an organic group, or a halogen atom,
$R^7$ is a hydrogen atom, an organic group, or a halogen atom, and
$R^8$ is a hydrogen atom, an organic group, or a halogen atom.

In the organic compound (1a), preferably, for example,
A is an aromatic group optionally having one or more substituents,
$R^1$ is a hydrogen atom or a $C_1$-$C_5$ alkyl group optionally having one or more substituents, and
$R^2$ is a hydrogen atom or a $C_1$-$C_5$ alkyl group optionally having one or more substituents.

In the organic compound (1b), preferably, for example,
$R^3$ is an alkyl group optionally having one or more substituents, —OR, or —NR$_2$,
$R^4$ is a hydrogen atom, a halogen atom, —OR, or —NR$_2$,
$R^5$ is an alkyl group optionally having one or more substituents, —OR, or —NR$_2$, and
R is independently at each occurrence a hydrogen atom or an organic group.

In the organic compound (1c), preferably, for example, B is an aromatic group optionally having one or more substituents,
$R^6$ is a hydrogen atom or a $C_1$-$C_5$ alkyl group,
$R^7$ is a hydrogen atom or a $C_1$-$C_5$ alkyl group, and
$R^8$ is a hydrogen atom or a $C_1$-$C_5$ alkyl group.

2.2. Target Product (Fluorinated Compound)

By the production method of the present invention, a fluorinated compound (1af) of the following formula is obtained corresponding to the organic compound (1a).

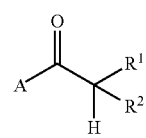
(1af)

(The symbols in the formula are the same as those in formula (1a).)

By the production method of the present invention, a fluorinated compound (1bf) of the following formula is obtained corresponding to the organic compound (1b).

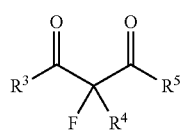
(1bf)

(The symbols in the formula are the same as those in the formula (1b).)

By the production method of the present invention, a fluorinated compound (1bf) of the following formula is obtained corresponding to the organic compound (1b).

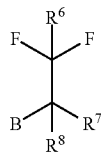

(1cf)

(The symbols in the formula are the same as those in the formula (1c).)

2.3. Step A

2.3.1. Hypervalent Iodine Aromatic Ring Compound (2a), Iodine Aromatic Ring Compound (2b), and Oxidant (Oxidant (2bo))

In step A, a hypervalent iodine aromatic ring compound (2a) or an iodine aromatic ring compound (2b) is used.

Specific examples of the hypervalent iodine aromatic ring compound (2a) include iodosylbenzene, 2-iodosyltoluene, 3-iodosyltoluene, 4-iodosyltoluene, 2,4,6-trimethyliodosylbenzene, 2-ethyliodosylbenzene, 3-ethyliodosylbenzene, 4-ethyliodosylbenzene, 2-iodosylanisole, 3-iodosylanisole, 4-iodosylanisole, 1-chloro-2-iodosylbenzene, 1-chloro-3-iodosylbenzene, 1-chloro-4-iodosylbenzene, 1,2-diiodosylbenzene, 1,3-diiodosylbenzene, 1,4-diiodosylbenzene, 1-iodosyl-2-nitrobenzene, 1-iodosyl-3-nitrobenzene, 1-iodosyl-4-nitrobenzene, 1-iodosyl-2-cyanobenzene, 1-iodosyl-3-cyanobenzene, and 1-iodosyl-4-cyanobenzene.

These can be used singly or in combination of two or more.

Examples of the iodine aromatic ring compound (2b) include iodobenzene, 2-iodotoluene, 3-iodotoluene, 4-iodotoluene, 2,4,6-trimethyliodobenzene, 2-ethyliodobenzene, 3-ethyliodobenzene, 4-ethyliodobenzene, 2-iodoanisole, 3-iodoanisole, 4-iodoanisole, 1-chloro-2-iodobenzene, 1-chloro-3-iodobenzene, 1-chloro-4-iodobenzene, 1,2-diiodobenzene, 1,3-diiodobenzene, 1,4-diiodobenzene, 1-iodo-2-nitrobenzene, 1-iodo-3-nitrobenzene, 1-iodo-4-nitrobenzene, 1-iodo-2-cyanobenzene, 1-iodo-3-cyanobenzene, 1-iodo-4-cyanobenzene, 1-iodo-4-(3,3,4,4,5,5,6,6,7,7,8,8,8-tridecafluorooctyl)benzene, p-iodobenzoic acid, 2-iodopyridine, 3-iodopyridine, 4-iodopyridine, 3-iodopyrazole, and 4-iodopyrazole.

These can be used singly or in combination of two or more.

In step A, the hypervalent iodine aromatic ring compound (2a) can be preferably used in the absence of an oxidant.

The phrase "in the absence of an oxidant" as mentioned herein may mean that the amount of oxidant in the reaction system of step A is 0.1 mol or less per mol of the organic compound (1).

In step A, the iodine aromatic ring compound (2b) is used together with an oxidant.

Examples of the oxidant (oxidant (2bo)) that can be used in step A include one or more members selected from the group consisting of metachloroperbenzoic acid, hydrogen peroxide, peracetic acid, perbenzoic acid, tert-butyl hydroperoxide, cumene hydroperoxide, potassium persulfate, and a potassium hydrogen persulfate-potassium hydrogen sulfate-potassium sulfate mixture.

These can be used singly or in combination of two or more.

The amount of the oxidant used in step A may be generally in the range of 0.1 to 20 mol per mol of the organic compound (1).

The hypervalent iodine aromatic ring compound (2a) is preferably a compound represented by formula (p1):

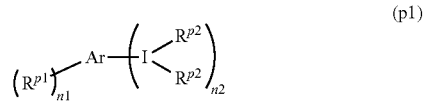

(p1)

wherein
Ar is an aromatic ring,
$R^{p1}$ is independently at each occurrence
  an alkyl group,
  an alkoxy group,
  a group: —O—$(CH_2)_q$—$NR_3X$, wherein q is a number greater than or equal to 1; R is H or a $C_1$-$C_{20}$ alkyl group; and X is a halogen atom, an arylsulfonyloxy group, or an alkylsulfonyloxy group,
  a group: —$(CH_2)_q$—$NR_3X$, wherein q is a number greater than or equal to 1; R is H or a $C_1$-$C_{20}$ alkyl group; and X is a halogen atom, an arylsulfonyloxy group, or an alkylsulfonyloxy group,
  a group: —O—$(CH_2)_q$-A, wherein A is —$SO_3Y$ or —COOY; Y is independently at each occurrence H, a metal atom (preferably sodium), or $NR^5_4$; and $R^5$ is independently at each occurrence H or an organic group (preferably methyl or ethyl),
  a group: —$(CH_2)_q$-A, wherein A is —$SO_3Y$ or —COOY; Y is independently at each occurrence H, a metal atom (preferably sodium), or $NR^5_4$; and $R^5$ is independently at each occurrence H or an organic group (preferably methyl or ethyl),
  a halogen atom,
  a cyano group,
  a nitro group,
  a carboxylic acid group, or
  a sulfonic acid group;
$R^{p2}$ is independently at each occurrence
  an alkyl group,
  an alkoxy group,
  a group: —O—$(CH_2)_q$—$NR_3X$, wherein q is a number greater than or equal to 1; R is H or a $C_1$-$C_{20}$ alkyl group; and X is a halogen atom, an arylsulfonyloxy group, or an alkylsulfonyloxy group,
  a group: —$(CH_2)_q$—$NR_3X$, wherein q is a number greater than or equal to 1; R is H or a $C_1$-$C_{20}$ alkyl group; and X is a halogen atom, an arylsulfonyloxy group, or an alkylsulfonyloxy group,
  a halogen atom,
  a cyano group,
  a nitro group,
  a carboxylic acid group,
  a sulfonic acid group,
  a hydroxy group, or
  a phosphoryloxy group; or
two $R^{p2}$ bonded to one iodine atom optionally together form =O;
n1 is a number greater than or equal to 0;
n2 is a number greater than or equal to 1; and
the sum of n1 and n2 is in the range of 1 to 11.

The iodine aromatic ring compound (1b) is preferably compound represented by formula (p1'):

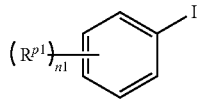 (p1')

wherein
Ar is an aromatic ring,
$R^{p1}$ is independently at each occurrence
 an alkyl group,
 an alkoxy group,
 a group: —O—$(CH_2)_q$—$NR_3X$, wherein q is a number greater than or equal to 1; R is H or a $C_1$-$C_{20}$ alkyl group; and X is a halogen atom, an arylsulfonyloxy group, or an alkylsulfonyloxy group,
 a group: —$(CH_2)_q$—$NR_3X$, wherein q is a number greater than or equal to 1; R is H or a $C_1$-$C_{20}$ alkyl group; and X is a halogen atom, an arylsulfonyloxy group, or an alkylsulfonyloxy group,
 a group: —O—$(CH_2)_q$-A, wherein A is —$SO_3Y$ or —COOY; Y is independently at each occurrence H, a metal atom (preferably sodium), or $NR^5_4$; and $R^5$ is independently at each occurrence H or an organic group (preferably methyl or ethyl),
 a group: —$(CH_2)_q$-A, wherein A is —$SO_3Y$ or —COOY; Y is independently at each occurrence H, a metal atom (preferably sodium), or $NR^5_4$; and $R^5$ is independently at each occurrence H or an organic group (preferably methyl or ethyl),
 a halogen atom,
 a cyano group,
 a nitro group,
 a carboxylic acid group, or
 a sulfonic acid group;
$R^{p2}$ is independently at each occurrence
 an alkyl group,
 an alkoxy group,
 a group: —O—$(CH_2)_q$—$NR_3X$, wherein q is a number greater than or equal to 1; R is H or a $C_1$-$C_{20}$ alkyl group; and X is a halogen atom, an arylsulfonyloxy group, or an alkylsulfonyloxy group,
 a group: —$(CH_2)_q$—$NR_3X$, wherein q is a number greater than or equal to 1; R is H or a $C_1$-$C_{20}$ alkyl group; and X is a halogen atom, an arylsulfonyloxy group, or an alkylsulfonyloxy group,
 a halogen atom,
 a cyano group,
 a nitro group,
 a carboxylic acid group,
 a sulfonic acid group,
 a hydroxy group, or
 a phosphoryloxy group; or
two $R^{p2}$ bonded to one iodine atom optionally together form =O; and
n1 is a number of 0 to 5.

In structure formula (p1), $R^{p1}$ is preferably independently at each occurrence
an alkyl group optionally substituted with one or more fluorine atoms,
an alkoxy group optionally substituted with one or more fluorine atoms,
a halogen atom,
a carboxylic acid group, or
a sulfonic acid group.

In structure formula (p1'), $R^{p1}$ is preferably independently at each occurrence
an alkyl group optionally substituted with one or more fluorine atoms,
an alkoxy group optionally substituted with one or more fluorine atoms,
a halogen atom,
a carboxylic acid group, or
a sulfonic acid group.

The number of fluorine atoms as substituents may be 1 to the maximum substitutable number. Specific examples thereof include 1, 2, 3, 4, 5, 6, 7, 8, and 9 fluorine atoms.

In structure formula (p1), $R^{p2}$ is preferably independently at each occurrence a halogen atom, an acetic acid group, a trifluoroacetic acid group, a tosic acid group, a hydroxy group, a phosphoryloxy group, a trifluoromethanesulfonic acid group, a propionic acid group, a 3,3,3-trifluoropropionic acid group, a perfluoropropionic acid group, a perfluorobutyric acid group, or a methanesulfonic acid group.

In the present specification, the term "acid group" may refer to an atom or atomic group remaining after one hydrogen atom that can be ionized as a hydrogen ion is removed from a molecule of an organic or inorganic acid.

Specifically, for example, in the present specification, the "carboxylic acid group" may include an "acetic acid group," and the "acetic acid group" may be —$OCOCH_3$ (an acetyloxy group).

2.3.2. Fluorine Source (3)

The fluorine source (3) used in step A may be:
a fluorine source (3a) represented by formula: $MF_n$, wherein M is H, a metal of Group 1 of the periodic table, or a metal of Group 2 of the periodic table; and n is 1 or 2,
the polymer (2cp), or
a combination thereof.

That is, when the $IF_2$-substituted aromatic ring-containing polymer (2cp) is used, the polymer (2cp) can also serve as the fluorine source (3).

M may be preferably H, Li, Na, K, Ca, or Cs; more preferably H, Na, K, or Ca; and even more preferably H.

The fluorine source may be preferably a hydrogen fluoride source.

Examples of the fluorine source include anhydrous hydrofluoric acid, a hydrofluoric acid aqueous solution (e.g., a hydrofluoric acid aqueous solution with a concentration of 10 to 70 wt %), and a mixture of hydrofluoric acid, an organic base, and an inorganic base.

In this mixture, the hydrofluoric acid and organic base may be specifically, for example, salts, such as hydrogen fluoride-triethylamine salt [$Et_3N$·nHF (n=1 to 5)], hydrogen fluoride-pyridine salt [Py·nHF (n=1 to 10)], and hydrogen fluoride-tetraethylammonium fluoride salt [$Et_4NF$·nHF (n=1 to 10)]; or may be derived therefrom.

In this mixture, the hydrofluoric acid and inorganic base may be specifically, for example, HF—KF($KHF_2$), or may be derived therefrom.

These fluorine sources can be used singly or in combination of two or more.

The amount of fluorine source used may be, for example, as hydrogen fluoride, generally in the range of 0.5 to 100 mol, preferably in the range of 1 to 80 mol, more preferably in the range of 2 to 60 mol, and even more preferably in the range of 3 to 50 mol, per mol of the organic compound (1), which is the substrate of the production method of the present invention.

The substrate of step A may be added to the reaction system of step A all at once, in several batches, or continuously.

2.3.3. Conditions of Step A

The reaction of step A can be carried out in the presence or absence of a solvent.

The solvent may be a non-polar solvent or a polar solvent.

Examples of the solvent include esters, ketones, aromatic compounds, alcohols, ethers, amines, nitrogen-containing polar organic compounds, nitriles, halogenated hydrocarbons, aliphatic hydrocarbons, fluorine-based solvents, carbonates, other solvents, and combinations thereof.

Examples of esters as the solvent include ethyl acetate, butyl acetate, amyl acetate, ethylene glycol monomethyl ether acetate, and propylene glycol monomethyl ether acetate; and preferably ethyl acetate.

Examples of ketones as the solvent include acetone, methyl ethyl ketone, diethyl ketone, hexanone, methyl isobutyl ketone, heptanone, diisobutyl ketone, acetonylacetone, methylhexanone, acetophenone, cyclohexanone, and diacetone alcohol; and preferably acetone.

Examples of aromatic compounds as the solvent include anisole, benzene, toluene, xylene, and ethylbenzene; and preferably benzene and toluene.

Examples of alcohols as the solvent include methanol, ethanol, n-propanol, isopropanol, n-butanol, pentanol, hexanol, ethylene glycol, diethylene glycol, triethylene glycol, tetraethylene glycol, polyethylene glycol, propylene glycol, dipropylene glycol, tripropylene glycol, polypropylene glycol, trimethylene glycol, and hexanetriol; and preferably methanol and ethanol.

Examples of ethers as the solvent include diethyl ether, dibutyl ether, tetrahydrofuran, tetrahydropyran, dioxane, dimethoxyethane, diethylene glycol diethyl ether, ethylene glycol monomethyl ether, ethylene glycol monoethyl ether, diethylene glycol monomethyl ether, diethylene glycol monoethyl ether, propylene glycol monomethyl ether (PGME; also known as "1-methoxy-2-propanol"), propylene glycol monoethyl ether, triethylene glycol dimethyl ether, triethylene glycol diethyl ether, tetraethylene glycol dimethyl ether, and tetraethylene glycol diethyl ether; and preferably diethyl ether and tetrahydro furan.

Examples of amines as the solvent include monoethanolamine, diethanolamine, and triethanolamine.

Examples of nitrogen-containing polar organic compounds as the solvent include N,N-dimethylformamide, N,N-dimethylacetamide, N-methyl-2-pyrrolidone, 2-pyrrolidone, and 1,3-dimethyl-2-imidazolidinone; and preferably N,N-dimethylformamide, N,N-dimethylacetamide, and N-methyl-2-pyrrolidone.

Examples of nitriles as the solvent include acetonitrile, propionitrile, butyronitrile, isobutyronitrile, benzonitrile, and adiponitrile; and preferably acetonitrile.

Examples of halogenated hydrocarbons as the solvent include dichloromethane, dichloroethane, chloroform, carbon tetrachloride, tetrachloroethane, trichloroethane, chlorobenzene, dichlorobenzene, and chlorotoluene; and preferably dichloromethane and chloroform.

Examples of aliphatic hydrocarbons as the solvent include hexane, cyclohexane, heptane, octane, nonane, decane, undecane, dodecane, and mineral spirits; and preferably cyclohexane and heptane.

Examples of fluorine-based solvents include perfluorobenzene, trifluorotoluene, ditrifluorobenzene, and trifluoroethanol; and preferably perfluorobenzene and trifluoroethanol.

Examples of carbonates as the solvent include tetralin dimethyl carbonate, methyl ethyl carbonate, diethyl carbonate, ethylene carbonate, and propylene carbonate; and preferably ethylene carbonate and propylene carbonate.

Examples of other solvents include acetic acid, pyridine, dimethylsulfoxide, sulfolane, and water.

These solvents can be used singly or in combination of two or more.

The amount of solvent used may be, for example, generally in the range of 0 to 200 parts by mass, preferably in the range of 0 to 100 parts by mass, and more preferably in the range of 0 to 50 parts by mass, per part by mass of the organic compound (1), which is the substrate of the production method of the present invention.

The temperature of step A may be generally in the range of −78 to 200° C., preferably in the range of −10 to 100° C., and more preferably in the range of 0 to 100° C.

The time of step A may be generally in the range of 0.1 to 72 hours, preferably in the range of 0.1 to 48 hours, and more preferably in the range of 0.1 to 36 hours.

2.4. Step B

The method of the present invention comprises step B of separating the iodine aromatic ring compound (2b) from the reaction liquid after step A is started.

The iodine aromatic ring compound (2b) may be an iodine aromatic ring compound generated from the hypervalent iodine aromatic ring compound (2a) in step A.

The separation may be generally performed after the start of step A, and is not necessarily performed after the reaction of step A is completely completed.

The separation may be performed by selecting an appropriate means, depending on the characteristics etc. of the iodine aromatic ring compound (2b).

Specifically, the recovery can be carried out, for example, by adding a basic aqueous solution (e.g., NaOH water) to the reaction liquid of step A, separating the aqueous layer by liquid separation, adding an acidic aqueous solution (e.g., HCl water) thereto, separating the organic layer by liquid separation, and then concentrating the solvent.

Specifically, the recovery can also be carried out, for example, by extracting the iodine aromatic ring compound (2b) with a suitable solvent (e.g., a fluorous solvent).

As a means for the separation, for example, a conventional method such as liquid separation or filtration can be used.

The conditions of step B may be set as appropriate based on common technical knowledge.

2.5. Step C

The method of the present invention preferably comprises step C of oxidizing the iodine aromatic ring compound (2b) separated from the reaction liquid with an oxidant (C).

The hypervalent compound generated by reoxidation in step C can be reused in step A.

The oxidant (C) may be preferably, for example, one or more members selected from the group consisting of:
a compound represented by formula: R$^x$COOOM
wherein R$^x$ is a hydrocarbon group optionally having one or more substituents, and
M is a hydrogen atom or a metal atom;
a compound represented by formula: R$^x$OOM
wherein R$^x$ is a hydrogen atom or a hydrocarbon group optionally having one or more substituents, and
M is a hydrogen atom or a metal atom; and
a metal oxide.

Examples of the oxidant (C) include metachloroperbenzoic acid, hydrogen peroxide, peracetic acid, perbenzoic acid, tert-butyl hydroperoxide, cumene hydroperoxide, potassium persulfate, a potassium hydrogen persulfate-potassium hydrogen sulfate-potassium sulfate mixture, permanganic acid, dichromic acid, tungsten oxide, ruthenium oxide, antimony oxide, osmium oxide, and sulfur trioxide.

Preferable examples of the oxidant (C) include metachloroperbenzoic acid, hydrogen peroxide, peracetic acid, perbenzoic acid, tert-butyl hydroperoxide, cumene hydroperoxide, potassium persulfate, and a potassium hydrogen persulfate-potassium hydrogen sulfate-potassium sulfate mixture.

More preferable examples of the oxidant (C) include m-chloroperbenzoic acid.

These can be used singly or in combination of two or more.

The amount of oxidant used in step C may be generally in the range of 0.1 to 20 parts by mass, preferably in the range of 0.5 to 20 parts by mass, and more preferably in the range of 0.6 to 10 parts by mass, per part by mass of the compound.

The oxidant is preferably m-chloroperbenzoic acid.

The conditions of step C may be set as appropriate based on common technical knowledge.

The target fluorinated organic compound obtained in this manner can be isolated or purified, if desired, by a conventional method, such as filtration, extraction, dissolution, concentration, precipitation, dehydration, adsorption, or chromatography, or a combination of these methods.

According to the present invention, the target product can be obtained in a yield of preferably 5 to 100, and more preferably 10 to 100.

According to the present invention, the hypervalent iodine aromatic ring compound or the iodine aromatic ring compound can be recovered with a recovery rate of preferably 10 to 100, and more preferably 20 to 100.

EXAMPLES

The present invention is described in more detail below with reference to Examples; however, the present invention is not limited thereto.

The meanings of the symbols and abbreviations in the Examples are shown below.
Py: pyridine Example 1 (Synthesis 1 of Ethyl Monofluorobenzoylacetate)

Ethyl benzoylacetate (1.0 mmol), p-iodobenzoic acid (0.2 eq.), dichloromethane (4 ml), Py·HF (20 eq. HF), and mCPBA (1.3 eq.) were added, and the mixture was stirred at room temperature for 24 hours. The reaction liquid was analyzed by F-NMR, and it was confirmed that the title target product was obtained in a yield of 18%.

On the other hand, NaOH water was added to the reaction liquid, and the aqueous layer was separated by liquid separation. HCl water was added thereto, and the organic layer was separated by liquid separation. Then, the solvent was concentrated, thereby recovering 88% of p-iodobenzoic acid.

Example 1-1 (Synthesis 1 of Ethyl Monofluorobenzoylacetate)

It was confirmed that the target product was obtained in a yield of 16% in the same manner as in Example 1, except that p-iodobenzoic acid was changed to the one recovered in Example 1. Further, 84% of p-iodobenzoic acid was recovered.

Example 2 (Synthesis 2 of Ethyl Monofluorobenzoylacetate)

Ethyl benzoylacetate (1.0 mmol), p-iodobenzoic acid (0.2 eq.), dichloromethane (4 ml), Py·HF (40 eq. HF), and mCPBA (1.3 eq.) were added, and the mixture was stirred at room temperature for 24 hours. The reaction liquid was analyzed by F-NMR, and it was confirmed that the title target product was obtained in a yield of 43%.

On the other hand, NaOH water was added to the reaction liquid, and the aqueous layer was separated by liquid separation. HCl water was added thereto, and the organic layer was separated by liquid separation. Then, the solvent was concentrated, thereby recovering 89% of p-iodobenzoic acid.

Example 2-1 (Synthesis 2 of Ethyl Monofluorobenzoylacetate)

It was confirmed that the target product was obtained in a yield of 40% in the same manner as in Example 2, except that p-iodobenzoic acid was changed to the one recovered in Example 2. Further, 88% of p-iodobenzoic acid was recovered.

Example 3 (Synthesis 3 of Ethyl Monofluorobenzoylacetate)

Ethyl benzoylacetate (1.0 mmol), N,N-diethyl-2-(3-iodophenoxy)ethan-1-amine (0.2 eq.), dichloromethane (4 ml), Py·HF (20 eq. HF), and mCPBA (1.5 eq.) were added, and the mixture was stirred at 40° C. for 24 hours. The reaction liquid was analyzed by F-NMR, and it was confirmed that the title target product was obtained in a yield of 70%.

On the other hand, ethyl acetate and water were added to the reaction liquid, and then the organic layer was separated by liquid separation. HCl water was added thereto, and then the aqueous layer was separated by liquid separation. NaOH water and ethyl acetate were added thereto, and then the organic layer was separated by liquid separation. Then, the solvent was concentrated, thereby recovering 23% of N,N-diethyl-2-(3-iodophenoxy)ethan-1-amine.

Example 3-1 (Synthesis 3 of Ethyl Monofluorobenzoylacetate)

It was confirmed that the target product was obtained in a yield of 65% in the same manner as in Example 3, except that N,N-diethyl-2-(3-iodophenoxy)ethan-1-amine was changed to the one recovered in Example 3. Further, 20% of N,N-diethyl-2-(3-iodophenoxy)ethan-1-amine was recovered.

Example 4 (Synthesis 4 of Ethyl Monofluorobenzoylacetate)

Ethyl benzoylacetate (1.0 mmol), N,N-diethyl-2-(3-iodophenoxy)ethan-1-amine (0.2 eq.), dichloromethane (4 ml), 55% HF water (28 eq. HF), and mCPBA (1.5 eq.) were added, and the mixture was stirred at 40° C. for 24 hours. The reaction liquid was analyzed by F-NMR, and it was confirmed that the title target product was obtained in a yield of 79%.

On the other hand, ethyl acetate and water were added to the reaction liquid, and then the aqueous layer was separated by liquid separation. NaOH water and ethyl acetate were added thereto, and then the organic layer was separated by liquid separation. Then, the solvent was concentrated, thereby recovering 20% of N,N-diethyl-2-(3-iodophenoxy)ethan-1-amine.

Example 4-1 (Synthesis 4 of Ethyl Monofluorobenzoylacetate)

It was confirmed that the target product was obtained in a yield of 75% in the same manner as in Example 4, except that N,N-diethyl-2-(3-iodophenoxy)ethan-1-amine was changed to the one recovered in Example 4. Further, 20% of N,N-diethyl-2-(3-iodophenoxy)ethan-1-amine was recovered.

Example 5 (Synthesis 5 of Ethyl Monofluorobenzoylacetate)

Ethyl benzoylacetate (1.0 mmol), 3-(3-iodophenoxy)-N,N-dimethylpropan-1-amine (0.2 eq.), dichloromethane (4 ml), Py·HF (20 eq. HF), and mCPBA (1.5 eq.) were added, and the mixture was stirred at 40° C. for 24 hours. The reaction liquid was analyzed by F-NMR, and it was confirmed that the title target product was obtained in a yield of 60%.

On the other hand, ethyl acetate and water were added to the reaction liquid, and then the organic layer was separated by liquid separation. HCl water was added thereto, and then the aqueous layer was separated by liquid separation. NaOH water and ethyl acetate were added thereto, and then the organic layer was separated by liquid separation. Then, the solvent was concentrated, thereby recovering 21% of 3-(3-iodophenoxy)-N,N-dimethylpropan-1-amine.

Example 5-1 (Synthesis 5 of Ethyl Monofluorobenzoylacetate)

It was confirmed that the target product was obtained in a yield of 55% in the same manner as in Example 3, except that 3-(3-iodophenoxy)-N,N-dimethylpropan-1-amine was changed to the one recovered in Example 5. Further, 20% of 3-(3-iodophenoxy)-N,N-dimethylpropan-1-amine was recovered.

Example 6 (Synthesis 6 of Ethyl Monofluorobenzoylacetate)

Ethyl benzoylacetate (1.0 mmol), m-iodosylphenylacetic acid (1.3 eq.), dichloromethane (4 ml), and 55% HF water (14 eq. HF) were added, and the mixture was stirred at 45° C. for 17 hours. The reaction liquid was analyzed by F-NMR, and it was confirmed that the title target product was obtained in a yield of 43%.

On the other hand, a sodium hydrogen carbonate aqueous solution and dichloromethane were added to the reaction liquid, and then the aqueous layer was separated by liquid separation. HCl water and dichloromethane were added thereto, and then the organic layer was separated by liquid separation. Then, the solvent was concentrated, thereby recovering 97% of m-iodophenylacetic acid.

Example 6-1 (Synthesis 6 of Ethyl Monofluorobenzoylacetate)

Ethyl benzoylacetate (1.0 mmol), the m-iodophenylacetic acid (0.2 eq.) recovered in Example 6, dichloromethane (2 ml), Py·HF (20 eq. HF), and mCPBA (1.5 eq.) were added, and the mixture was stirred at 40° C. for 24 hours. The reaction liquid was analyzed by F-NMR, and it was confirmed that the title target product was obtained in a yield of 50%.

On the other hand, a sodium hydrogen carbonate aqueous solution and dichloromethane were added to the reaction liquid, and then the aqueous layer was separated by liquid separation. HCl water and dichloromethane were added thereto, and then the organic layer was separated by liquid separation. Then, the solvent was concentrated, thereby recovering 95% of m-iodophenylacetic acid.

The invention claimed is:
1. A method for producing a fluorinated organic compound, comprising:
   step A of fluorinating an organic compound (1) by reaction with a fluorine source (3)
   in the presence of a hypervalent iodine aromatic ring compound (2a), or
   in the presence of an iodine aromatic ring compound (2b) and an oxidant (2bo);
   wherein the fluorine source (3) is a fluorine source (3a) represented by formula: $MF_n$, wherein M is H, a metal of Group 1 of the periodic table, or a metal of Group 2 of the periodic table; and n is 1 or 2;
   step B of separating the iodine aromatic ring compound from a reaction liquid after step A is started; and
   step C of oxidizing the iodine-substituted aromatic ring compound separated from the reaction liquid in step B with an oxidant (C),
wherein the organic compound (1) is:
   an organic compound represented by formula (1a):

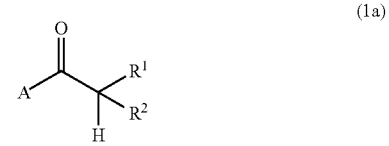

(1a)

wherein
A is a hydrogen atom, an aromatic group optionally having one or more substituents, an alkyl group optionally having one or more substituents, a halogen atom, —OR, or —NR$_2$,
R$^1$ is a hydrogen atom, an organic group, or a halogen atom,
R$^2$ is a hydrogen atom, an organic group, or a halogen atom, and R is independently at each occurrence a hydrogen atom or an organic group; or an organic compound represented by formula (1b):

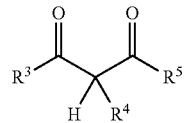

wherein
$R^3$ is a hydrogen atom, an aromatic group optionally having one or more substituents, an alkyl group optionally having one or more substituents, a halogen atom, —OR, or —NR$_2$,
$R^4$ is a hydrogen atom, an aromatic group optionally having one or more substituents, an alkyl group optionally having one or more substituents, a halogen atom, —OR, or —NR$_2$,
$R^5$ is a hydrogen atom, an aromatic group optionally having one or more substituents, an alkyl group optionally having one or more substituents, a halogen atom, —OR, or —NR$_2$, and
R is independently at each occurrence a hydrogen atom or an organic group; and
  wherein the hypervalent iodine aromatic ring compound (2a) is an organic compound represented by formula (2a1):

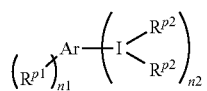

wherein
Ar is an aromatic ring,
$R^{p1}$ is independently at each occurrence
  a group: —O—$(CH_2)_q$—NR$_3$X, wherein q is a number greater than or equal to 1; R is H or a $C_1$-$C_{20}$ alkyl group; and X is a halogen atom, an arylsulfonyloxy group, or an alkylsulfonyloxy group,
  a group: —$(CH_2)_q$—NR$_3$X, wherein q is a number greater than or equal to 1; R is H or a $C_1$-$C_{20}$ alkyl group; and X is a halogen atom, an arylsulfonyloxy group, or an alkylsulfonyloxy group,
  a group: —O—$(CH_2)_q$-A, wherein q is a number greater than or equal to 1; A is —SO$_3$Y or —COOY; Y is independently at each occurrence H, a metal atom, or NR$^5$$_4$; and $R^5$ is independently at each occurrence H or an organic group,
  a group: —$(CH_2)_q$-A, wherein q is a number greater than or equal to 1; A is —SO$_3$Y or —COOY; Y is independently at each occurrence H, a metal atom, or NR$^5$$_4$; and $R^5$ is independently at each occurrence H or an organic group,
  a carboxylic acid group, or
  a sulfonic acid group;
$R^{p2}$ is independently at each occurrence
  an alkyl group,
  an alkoxy group,
  a group: —O—$(CH_2)_q$—NR$_3$X, wherein q is a number greater than or equal to 1; R is H or a $C_1$-$C_{20}$ alkyl group; and X is a halogen atom, an arylsulfonyloxy group, or an alkylsulfonyloxy group,
  a group: —$(CH_2)_q$—NR$_3$X, wherein q is a number greater than or equal to 1; R is H or a $C_1$-$C_{20}$ alkyl group; and X is a halogen atom, an arylsulfonyloxy group, or an alkylsulfonyloxy group,
  a halogen atom,
  a cyano group,
  a nitro group,
  a carboxylic acid group,
  a sulfonic acid group,
  a hydroxy group, or
  a phosphoryloxy group; or
two $R^{p2}$ bonded to one iodine atom optionally together form =O;
n1 is a number greater than or equal to 1;
n2 is a number greater than or equal to 1; and
the sum of n1 and n2 is in the range of 2 to 11; and
  the iodine aromatic ring compound (2b) is an organic compound represented by formula (2b1):

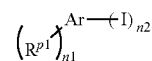

wherein
Ar is an aromatic ring;
$R^{p1}$ is independently at each occurrence
  a group: —O—$(CH_2)_q$—NR$_3$X, wherein q is a number greater than or equal to 1; R is H or a $C_1$-$C_{20}$ alkyl group; and X is a halogen atom, an arylsulfonyloxy group, or an alkylsulfonyloxy group,
  a group: —$(CH_2)_q$—NR$_3$X, wherein q is a number greater than or equal to 1; R is H or a $C_1$-$C_{20}$ alkyl group; and X is a halogen atom, an arylsulfonyloxy group, or an alkylsulfonyloxy group,
  a group: —O—$(CH_2)_q$-A, wherein q is a number greater than or equal to 1; A is —SO$_3$Y or —COOY; Y is independently at each occurrence H, a metal atom, or NR$^5$$_4$; and $R^5$ is independently at each occurrence H or an organic group,
  a group: —$(CH_2)_q$-A, wherein q is a number greater than or equal to 1; A is —SO$_3$Y or —COOY; Y is independently at each occurrence H, a metal atom, or NR$^5$$_4$; and $R^5$ is independently at each occurrence H or an organic group,
  a carboxylic acid group, or
  a sulfonic acid group;
n1 is a number greater than or equal to 1;
n2 is a number greater than or equal to 1; and
the sum of n1 and n2 is in the range of 2 to 11.

2. The production method according to claim 1, wherein $R^{p1}$ in formulas (2a1) and (2b1) is independently at each occurrence a carboxylic acid group, or a sulfonic acid group.

3. The production method according to claim 1, wherein $R^{p2}$ in formula (2a1) is independently at each occurrence a halogen atom, an acetic acid group, a trifluoroacetic acid group, a tosic acid group, a hydroxy group, a phosphoryloxy group, a trifluoromethanesulfonic acid group, a propionic acid group, a 3,3,3-trifluoropropionic acid group, a perfluoropropionic acid group, a perfluorobutyric acid group, or a methanesulfonic acid group.

4. The production method according to claim 1, wherein the oxidant (2bo) is one or more members selected from the group consisting of metachloroperbenzoic acid, hydrogen peroxide, peracetic acid, perbenzoic acid, tert-butyl hydroperoxide, cumene hydroperoxide, potassium persulfate, and a potassium hydrogen persulfate-potassium hydrogen sulfate-potassium sulfate mixture.

5. The method according to claim 1, wherein the oxidant (C) is one or more members selected from the group consisting of metachloroperbenzoic acid, hydrogen peroxide, peracetic acid, perbenzoic acid, tert-butyl hydroperoxide, cumene hydroperoxide, potassium persulfate, and a potassium hydrogen persulfate-potassium hydrogen sulfate-potassium sulfate mixture.

* * * * *